United States Patent [19]

Malcolm et al.

[11] Patent Number: 4,979,198
[45] Date of Patent: Dec. 18, 1990

[54] METHOD FOR PRODUCTION OF FLUOROSCOPIC AND RADIOGRAPHIC X-RAY IMAGES AND HAND HELD DIAGNOSTIC APPARATUS INCORPORATING THE SAME

[76] Inventors: David H. Malcolm, 18 Deer Run Dr., Randolph, N.J. 07869; George P. T. Wilenius, RR #1, Dunrobin, Ontario, Canada, K0A 1T0

[21] Appl. No.: 375,124

[22] Filed: Jul. 3, 1989

Related U.S. Application Data

[63] Continuation of Ser. No. 224,121, Jun. 20, 1988, which is a continuation of Ser. No. 863,318, May 15, 1986.

[51] Int. Cl.$^5$ .............................. H05G 1/10
[52] U.S. Cl. .................. 378/102; 378/181; 378/190; 378/198
[58] Field of Search ............. 378/101, 102, 109–113, 378/116, 181, 189–192, 210

[56] References Cited

U.S. PATENT DOCUMENTS

| | | | |
|---|---|---|---|
| 1,961,705 | 6/1934 | Mutscheller | 378/109 |
| 4,142,101 | 2/1979 | Yin | 378/102 |
| 4,856,036 | 8/1989 | Malcolm et al. | 378/116 |

Primary Examiner—Craig E. Church

[57] ABSTRACT

Method and apparatus for the production of fluoroscopic and radiographic x-ray images utilizing a portable hand-held and battery operated x-ray system. The system incorporates a unique high voltage power supply of diminutive size and weight which may be disposed totally within the hand-held system. By utilizing the system in conjunction with a currently available hand operated instant Polaroid film developer, the system provides total portability and field operability in both fluoroscopic and radiographic mode.

8 Claims, 5 Drawing Sheets

METHOD FOR PRODUCTION OF FLUOROSCOPIC AND RADIOGRAPHIC X-RAY IMAGES AND HAND HELD DIAGNOSTIC APPARATUS INCORPORATING THE SAME

This is a continuation of application Ser. No. 224121 filed June 20, 1988, which was a continuation of Ser. No. 863,318 filed May 15, 1986.

This invention relates to improved method and apparatus for the selective production of fluoroscopic or radiographic x-ray images for diagnostic purposes in a readily portable, hand-held and battery powered x-ray system.

Many devices employing x-rays or other types of radiation have been used and/or proposed for use to produce fluoroscopic or transitory images and radiographic images for diagnostic purposes. The majority of such devices are of bulky and heavy character and are either fixed in location or rendered mobile by using special carts to permit limited movement thereof. Most of such units, by their nature, produce large dosage of x-rays and consume large amounts of power necessitating specialized electrical power sources and, for mobil units, heavy and bulky arrays of batteries. Illustrative of such mobile units are the General Electric Polarix and Fisher Omni 325 systems which weigh in excess of 600 lbs. and require 220 volt power at up to 70 amperes or equivalent battery packs. Other manufactures supply generally similar units.

In recent years, various diagnostic systems have been advanced which offer increased mobility and, in at least one case, portability, with the latter being attended by sacrifice of performance capability and versatility. These latter systems include the Healthmate Fluoroscan, the Lixiscope and the Bowie portable unit, the latter being specifically intended for veterinary application. The Healthmate Fluoroscan and the Lixiscope, which both employ microchannel plate image intensifiers, are purportedly licensed under U.S. Pat. No. 4,142,101 and function only as fluoroscopes. The Healthmate, Bowie and Lixiscope weigh respectively 200 pounds, 21 pounds and 5 to 8 pounds with the first two being operable from standard 115 VAC line power. Both the Fluoroscan and Bowie unit utilize x-rays while the Lixiscope utilizes gamma-rays from a radioactive isotope source. Such gamma ray usage requires special handling and the replacement of the source at three to six month intervals as the isotope decays.

A matter of concern in any diagnostic process utilizing x-rays or gamma rays is the potential for biological damage to the patient and the hazards presented to the operator of the device. Most x-ray systems currently in use for both fluoroscopy and radiography utilize high intensity x-radiation, which high intensity is dictated, in large part, by the relatively low gain or limited degree of light amplification provided by conventional image intensification techniques and also by the relatively long source to image distances employed in such systems. The high radiation intensities employed in these systems also require the use of x-ray tubes employing large area focal spots since otherwise the high beam currents would generate too much heat and lead to rapid deterioration of the tube anode. X-ray tubes employing large area focal spots necessitate operation at long source to image distances in order to maintain satisfactory image resolution or definition.

This invention may be briefly described, in its broad aspects, as improved method and apparatus techniques for x-ray fluoroscopic and radiographic imaging. Improved apparatus constructed in accord with the principles of this invention broadly includes a small, portable, hand-held x-radiation generating and imaging means suitable for both fluoroscopic and/or radiograhic operation, at the option of the user, powered by a small battery and in which small focal spot x-ray tube areas are employed and the source to image receptor distance is markedly reduced. In a narrower aspect, such apparatus is desirably in the form of a C-shaped housing containing a small focal spot x-ray tube and shielding assembly with beam collimation and directing means situated at the end of one arm of the C shaped housing. A small sized high voltage DC power supply is located immediately adjacent the x-ray tube housing assembly. Low voltage power control circuitry and monitoring devices are located within the center portion of the C-arm assembly. The other arm of the C shaped housing disposed opposite that containing the x-ray head assembly may be used as a handle for the device and preferably contains switch mechanisms to control the production of x-rays. Mounted at the end of the second arm portion of the C shaped housing are interchangeable means for producing enhanced fluoroscopic or radiographic images of objects disposed between the two extremities of the C-arm assembly. In a still narrower aspect the invention includes effecting radiographic imaging of an interposed object by utilizing a cassette suitably retained in a tray mechanism rigidly attached to the second or handle end of the C-arm assembly. Such cassettes contain sensitive screens which emit visible light when exposed to x-radiation. Such visible light emissions are utilized to produce a photographic image on a conventional negative film or an instant Polaroid positive film. Fluoroscopic imaging is conveniently effected using a similar type of x-ray sensitive screen, and amplifying the brightness of the emitted visible image by suitable high gain light intensification means, preferably of microchannel plate configuration. Optical coupling means which may contain magnification or minification components may be be interposed between the x-ray image receptor screen and the image intensifying means and between the output screen of the image intensifier and the viewing screen or lens.

The primary object of this invention is the provision of improved method and apparatus for x-radiation fluoroscopic and radiographic imaging employing markedly reduced radiation levels.

Another object of this invention is the provision of small sized, light weight and readily portable fluoroscopic and/or radiographic x-ray imaging apparatus particularly adapted for use as a diagnostic tool for the viewing of non-torso extremities, such as hands, arms and legs.

Another object of this invention is the provision of improved fluoroscopic and/or radiographic x-ray imaging techniques in which the source to image receptor distance is markedly reduced and small x-ray tube focal spots are employed.

A futher object of this invention is the provision of improved techniques for fluoroscopic and/or radiographic x-ray imaging, that markedly reduce the needed electrical power requirements for operation thereof.

Referring to the drawing.

Figure 1:
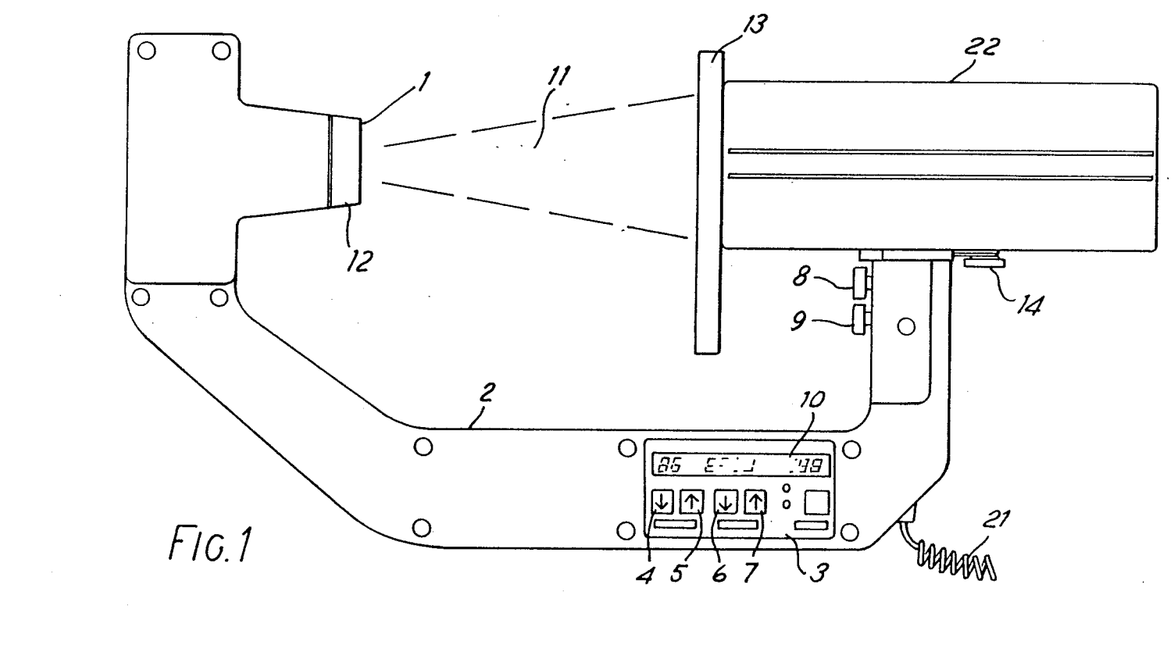
FIG. 1 is a schematic side elevational view of a preferred configuration of a low intensity x-ray system for operation in the fluoroscopic mode incorporating the principles of this invention.
Figure 2:
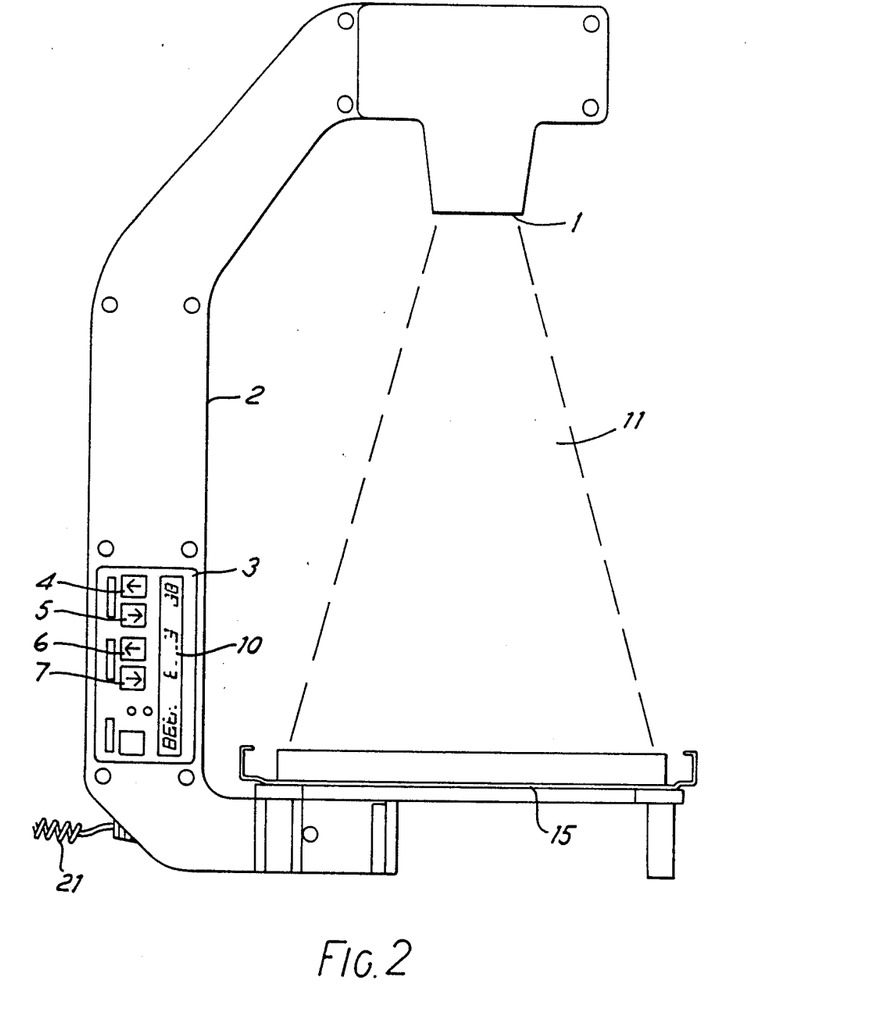
FIG. 2 is a schematic side elevational view of the apparatus of FIG. 1, as adapted for operation in the radiographic mode.
Figure 3:
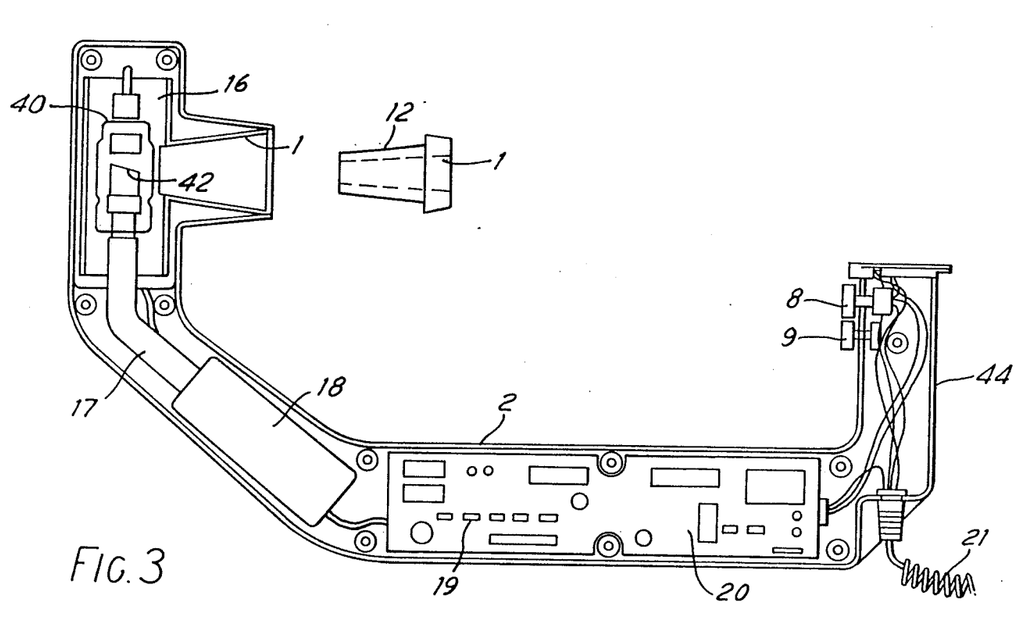
FIG. 3 is a vertical sectional view of the low intensity x-ray system shown in FIG. 1 showing the positioning of major components therein.

Referring now to FIGS. 1, 2 and 3 there are illustrated exemplary components of a low intensity hand portable embodiment of an x-ray imaging device capable of both fluoroscopic and radiographic imaging at the option of the user that incorporates the principles of this invention. As shown, x-radiation is emitted through a collimating cone 1 located near the end of one of the arms of the C-arm assembly 2. A control panel 3 containing mode and level switches 4, 5, 6 and 7 permits x-radiation to be emitted at predetermined selected levels of voltage and intensity for either mode of operation upon actuation of one or both of the actuating buttons 8 and 9. The pre-set levels of voltage and x-ray beam current together with various information pertaining to exposure time are presented on a display panel 10 preferably of a liquid crystal character, which may be back illuminated for improved visibility. Preferably a microprocessor control system is included in the device and the display panel 10 may also be utilized to direct other information and error conditions, such as low battery power, to the attention of the operator.

In the fluoroscopic mode of operation as depicted in FIG. 1, the spread or divergence of the emitted x-ray beam 11 is further reduced by the addition of a beam limiter 12 to the collimator cone assembly 1. The spread of the x-ray beam is controlled and limited so that the fluoroscopic image receptor assembly 22 effectively intercepts all of the emitted x-ray beam 11 to thereby minimize, if not avoid, exposure of the operator to the emitted radiation. An additional shield 13, preferably of leaded plastic material, may also be mounted on the image receptor assembly 22 surrounding the aperture therein to further protect the operator from the fringe portions of the emitted radiation and leakage and scatter radiation. The shield 13 is selectively shaped to especially protect the eyes, thyroid and hand of the user. The device is preferably constructed so that the fluoroscopic image receptor assembly 22 may be easily and readily removed by loosening a knurled screw 14 and replaced with a radiographic cassette holder tray 15 as shown in FIG. 2, for operation in the radiographic mode to produce permanent film records at the option of the user. Suitable protective interlock mechanisms are incorporated to prevent operation in such manner as might be dangerous to patient or operator. For example, one interlock renders the unit inoperable if the beam limiter is not positioned in place when operating in the fluoroscopic mode, or if the image receptor head is not properly positioned under either mode of operation. Also included are means responsive to the selected positioning of the first image producing means in predetermined spatial relation with the radiation source for limiting the x-ray tube electron beam current to a value intermediate 50 microamperes and 300 microamperes for fluoroscopic operation and means responsive to the selected positioning of the second image producing means in predetermined spatial relation with said radiation source for limiting the x-ray tube electron beam current to a value intermediate 500 microamperes and 3 milliamperes for radiation responsive photographic operation. Such protective interlocks are most readily and desireably accomplished by means of a microprocessor control system. Still another interlock or microprocessor control may operate to prevent system operation in the radiographic mode when the beam limiter 12 is in place since, under such condition, the resulting film record would show only the central portion of the image, necessitating a retake without the beam limiter 12 with consequent additional exposure of the patient to radiation.

Referring now to FIG. 3, there is illustrated a preferred arrangement of the major system components within the C-arm housing 2. As shown, the x-ray tube housing assembly 16 is located within one extremity of the C-arm assembly 2. Positioned in fixed spatial relation thereto by locating pins or other appropriate means, not shown, is a collimating cone 1. The beam limiter 12 is complementally shaped and sized to accomodate insertion thereof within the cone 1 in such manner that the axis of the narrowed conical beam passing therethrough is coaxial with the central axis of the generally rectangular collimating cone 1. As discussed above, when the beam limiter 12 is properly positioned within the cone 1, a detector mechanism, preferably in the nature of a small microswitch, or a magnetic position detecting means, is activated to provide a positive signal indicative of the beam limiters 12 presence to a microprocessor or other centralized control system. Disposed within the housing 16 is a small focal spot x-ray tube 40, suitably a Eureka EXR-80-20D. The x-ray tube housing assembly 16 is oil filled and preferably employs other high dielectric strength solid insulating materials, such as Kapton or Stycast 2850 FT, for electrical insulation purposes. Such tube housing assembly includes means to accurately position the focal spot on the x-ray tube target anode on the axis of the collimating cone 1.

High voltage power is fed to the x-ray tube anode 42 which is preferably disposed at the lower end of the tube housing assembly 16, through a high voltage connector assembly 17. The tube housing assembly 16 and the adjacent portion of the high voltage connector assembly 17 are surrounded by a suitable thickness of lead shielding, typically about 1 millimeter in thickness in the vicinity of the anode of the x-ray tube and with a reduced thickness to as little as 0.15 mm around the connector assembly 17. An x-ray window of suitable size is provided in the lead shield. The material constituting the cylindrical x-ray tube housing assembly 16 is preferably aluminum, typically about 0.5 mm in thickness which, together with the oil and other solid insulating materials contained therein and the glass of the x-ray tube provides sufficient filtration of low voltage or low energy x-radiation to maintain good beam quality. Such low energy radiation emission within the primary beam not only has insufficient penetrating power for good diagnostic purposes, but also may cause harmful effects to the patient.

The high voltage power supply 18 is desirably located immediately adjacent the high voltage connector assembly 17 in order to minimize high voltage leakage and transmission problems, and also to minimize possible interference caused by exposure of high voltages on nearby low voltage electronic components in the system. In order to minimize static build up and high voltage noise, all high voltage systems are encased within a grounded conducting shield which may suitably be a conducting paint similar to that used on the inside of computer cabinets and the like.

The low voltage electronic power amplifying system 19 and associated control system 20 are conveniently located in the elongated central portion of the C-arm housing 2 as shown in FIG. 3. The low voltage power amplifier system 19 is preferably disposed between the high voltage power system 18 and the microprocessor control system 20 since, especially when operated in radiographic mode, the high power level signals emanating from the power amplifier system 19 are transmitted directly to the adjacent high voltage power supply 18 and thereby minimize interference with the sensitive microprocessor system 20.

The end portion 44 of the second arm of the C-arm housing 2 is conveniently utilized as a handle for operation in the fluoroscopic mode and for containing the manual actuation switches 8 and 9 and audible warning transducers if such are desired. Power from an external battery pack, not shown, is introduced via the multiwire cable assembly 21.

Figure 4:
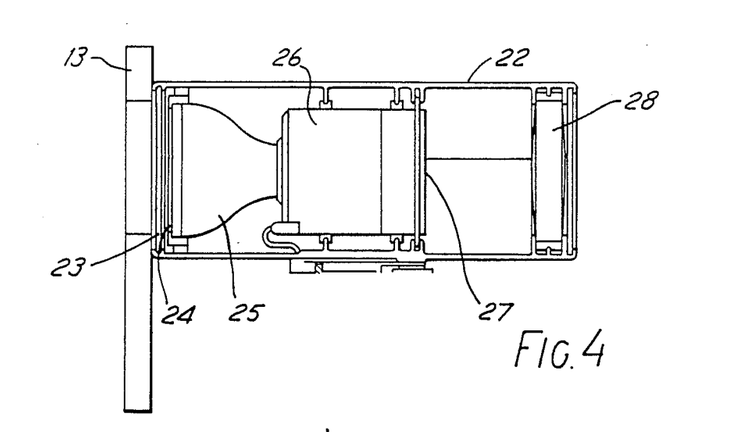
FIG. 4 is a vertical section of a preferred fluoroscopic imaging receptor assembly incorporating the principles of this invention.

Referring now to FIG. 4, there are illustrated exemplary components constituting a fluoroscopic imaging receptor assembly 22. As there shown, incident x-radiation after emission from the x-ray source and passage through an interposed examination subject, impinges upon and, passes through an optically opaque but x-ray transparent window 23 at the front of the receptor assembly 22. The window 23 may be fabricated from black plastic material such as Delrin and the portion thereof in the path of incident x-radiation is of small thickness, typically less than 1 mm. Disposed immediately behind the window 23 is a high resolution x-ray sensitive screen 24 of Kodak Lanex or similar material which converts the image defined by invisible incident x-radiation to an optically visible image, albeit of very low light intensity. The visible light producing screen 24 is disposed in immediate interfacial optical contact with the front face of a fiber optic cone assembly 25. Such interfacial optical contact may be enhanced by appropriate optical bonding materials or by depositing the active screen ingredients directly on the face of the cone 25. The fiber optic cone assembly 25 operates to efficiently transmit the low intensity visible image produced on the screen 24 to the input window of an image intensifier assembly 26. Desirably the output face of the fiber optic cone 25 is disposed in good optical contact with the image intensifier input window to minimize transmission losses therebetween. If desired, the visible image producing screen and the input window of the image intensifier may be coupled directly, or other optical transmission systems employing lenses may be interposed therebetween. The use of fiber optics or lenses permits controlled magnification or minification of the image thus permitting utilization of a larger or smaller field of view than the diameter of the image intensifier tube assembly. Care should be taken to maintain the entire screen 24 and the optical input assembly to the image intensifier light tight to prevent undesired degradation of the faint image produced by action of incident x-rays on the screen 24.

The image intensifier assembly 26 is preferably of microchannel plate construction which provides high light amplification, small size and has low power requirements. The image intensifier assembly 26 produces a bright visible image, conforming to the incident x-ray image, on the output screen 27. The image on the output screen 27 may be viewed directly or through suitable magnifying optical means 28 or, alternatively, as the output side of a second fiber optic cone assembly.

Lead shielding is disposed inside the image receptor housing 22 surrounding the optical image path to prevent unnecessary incident radiation from penetrating the image receptor assembly and to minimize operator exposure to radiation. As before noted, a shield 13, preferably transparent lead plastic, may be added to reduce to a minimum any radiation by-passing the image receptor and reaching the operator.

Figure 5:
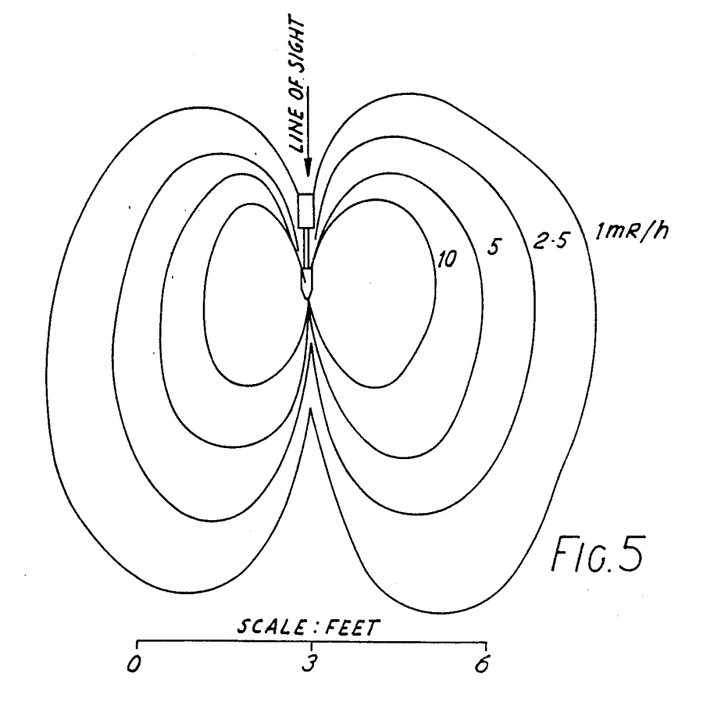
FIG. 5 is a plot of scatter radiation from a fluoroscopic low intensity imaging system embodying the principles of this invention.

FIG. 5 shows typical low radiation level contours produced by scatter from the examination subject and leakage from various components of the system, when operated in the fluoroscopic mode. Operation of small-sized portable x-ray diagnostic devices of the type described above antithetically requires the maintainance of low levels of radiation, both in the primary beam and also in the area of leakage and scatter, together with the provision of images of sufficient clarity to permit utilization of the unit as a safe diagnostic tool. Within the latter area a critical performance requirement is the resolution or the ability of the system to distinguish detail. To be an acceptable and practical diagnostic tool, the resolution of the system, in both fluoroscopic and radiographic modes, should be at least 3.5 line pairs per mm and preferably 5 line pairs per millimeter. Since the above described optical and fiber optical components have a resolving power considerably in excess of this level, it is necessary to ensure that the image defining detail of the emitted x-ray beam and the resolving capacity of the screen produce an initial visible image that is of high resolution and is above the threshold of intensity level that the image intensifier requires to maintain resolution to the required levels in the optically enhanced image.

As stated previously, we have found it desirable to use a microchannel plate image intensification system, not only because of its high gain, small size and low power characteristics, but also because such image intensification is capable, when operated with suitable input light levels, of resolution in the order of 30 line pairs per millimeter which permits, for example, magnification and/or minification by a factor of three while still providing inherent resolution level of 10 line pairs per mm. Such resolution capabilities permits the use of a relatively small and inexpensive image intensifier suitably having a 25 mm screen and viewing area, adopted to be used with fiber optic cones or lenses to provide a 75 mm viewing field in fluoroscopic mode. Such a viewing field accomodates the non-torso extremities such as feet and hands., which is a primary area of intended usage for the above described device.

A prime operating requirement is to ensure that the inherent resolution of the x-ray generation system is capable of an ultimate system resolution in excess of 5 line pairs per millimeter. As hereinbefore stated, this invention is directed to a hand-held portable x-ray generating system. As such, the attendant physical constraints in size and weight dictate that the x-ray source to image receptor distance is markedly less than that employed in conventional diagnostic x-ray apparatus and practically should not exceed about 50 centimeter. Such small x-radiation source to image distances in conjunction with an x-ray source focal spot of conventional size inherently leads to loss of image definition. Such small distance also inherently requires that the subject being examined is disposed undesirably close to the x-radiation source, where the radiation intensity is a maximum. To accomodate these divergent requirements the subject apparatus employs a minimum source to image receptor distance of 25 centimeters and preferably uses a source to image receptor spacing in the range 30 to 35 centimeters. Such reduced source to image receptor distances require selective utilization of a markedly reduced size of focal spot in the x-ray tube to maintain the desired degree of resolution. In order to realize the desired objectives we have determined that the focal spot should not desirably exceed 0.5 mm by 0.5 mm and certainly should be no larger than 1 mm by 1 mm.

As will be now apparent from the foregoing, a paramount operating requirement for hand-held portable x-ray systems as described herein is the preservation and maintanence of high resolution for both the fluoroscopic and radiographic mode of operation. Such high resolution can only be maintained, by selective utilization of a high resolution screen, such as Kodak Lanex, for the initial conversion of image defining x-radiation to visible light. Such type of high resolution screen requires a relatively high level of radiation to produce an image of acceptable brightness. In accord therewith a certain minimum level of transmitted x-radiation must be received at the screen to produce a visible image of acceptable resolution. For operation in fluoroscopic mode using a high resolution screen, such as Kodak Lanex, we have determined that subject free minimum radiation levels of 0.15 Roentgen per min (R/min) at the screen surface are necessary to provide required image quality, and preferably a radiation level that is in excess of 0.4 R/min. No substantial advantage is observed by further increasing screen radiation levels and, to minimize the potential for biological damage, an operating level of 2.0 R/min at the screen, without attenuation by passage of the radiation through the subject being examined, should not be exceeded for operation of a device constructed according to the principles of this invention. In the radiographic mode of operation, the radiation levels at the film cassette, without attenuation by objects interposed between the source and screen, are desirably between 2.5 R/min and 15 R/min, with a preferred value of 5 R/minute. In this latter case of radiographic operation, it will be apparent to those skilled in the art that such radiation levels depend substantially on exposure times and, accordingly, the above recommendations are based on maximum exposure times consistent with producing a distinct image of an extremity of a conscious human subject with said extremity supported by the film cassette. We have found that exposure times between 50 milliseconds and 3 seconds, but preferably in the order of from 50 millisecond to 1 second, generally provide acceptable images. The utilization of shorter exposure times and higher radiation levels, while not exposing the patient to more total radiation, has been found impractical for usage in a portable battery operated system of the type being described because of the size of the electronic power systems required.

It is well known to those practiced in the diagnostic arts, that the examination of human extremities and other objects of similar density require utilization of x-radiation of a certain energy content or penetrating power. It is well understood in the field that x-rays produced by application of peak voltages of between 35 kilovolts and 80 kilovolts and preferably in the range of from 40 to 75 kilovolts are suitable for this purpose when using fluoroscopy and somewhat lower levels are necessary when using radiography, where compensation to some extent may be made by variation in exposure time of the film cassette. Emitted x-radiation intensities are dependent upon both the peak kilovolts applied to the anode of the x-ray tube and also upon the level of electron beam current flowing from the x-ray tube filament to the anode thereof. Based upon the herein specified operating radiation levels and the applied peak kilovolts necessary for the contemplated diagnositc examination of various extremites, we have determined that a necessary range of electron beam current in the x-ray tube of from 50 to 300 microamps in the fluoroscopic mode will provide, in a device of the type described herein, a practical range for optimum operation. A preferred range of operation for maximum performance and safety is with tube currents of between 100 and 200 microamps. When operating in the radiographic mode a minimum beam current of 500 microamps and maximum of 3 milliamps is required, though the preferred range for optimum operating characteristics consistent with the portable nature of the system is between 750 microamps and 1.5 milliamps.

In order to minimize the level of radiation exposure to which the patient and operator may be exposed it is normally necessary to employ x-radiation impervious mechanical barrier means to prevent the close approach of body parts to the x-radiation source where said radiation intensities, due to the governing inverse square laws, become very high. In addition, the Federal Food and Drug Administration requires various forms of warnings, including audible alarms, when a fluoroscope is operated in any mode where possible skin exposure level exceeds 5 R/min. The provision of limiting barrier means of excessive length clearly intrudes on the physical space available to interpose bulkier body parts such as knees and shoulders. Means are included in the disclosed device to prevent source to skin distances of less than 6.5 cm and to normally operate at a minimum source to skin distance of 10 cm in a fluoroscopic mode. Such level of source to skin distances typically results in limiting skin exposure to less than 20 R/min. under normal operating conditions as heretofor described.

A primary practical concern in the efficient operation of portable battery operated x-ray imaging systems of the character herein described is the efficiency of conversion of source battery power to operating high voltage power. In typical fluoroscopic operation the required high voltage power levels are in the range of 10 to 30 watts and in the radiographic mode, required high voltage power levels are about five times higher, although in this latter case such high power levels are required for periods of very short duration. The efficiency of power conversion in such operation impacts not only upon battery life but also upon the amount of heat that is dissipated in the electronic components. At a 15 watt power level output an amplifier system operating at 20% efficiency must dissipate 60 watts as heat whereas an efficient system operating at 80% efficiency dissipates less than 4 watts in the form of heat. Inefficient modes of operation therefore generally require special and bulky heat dissipation adjuncts, as well as adversely affecting the basic reliability of the electronic systems. Conventional readily available electronic power amplifier systems operate at a theoretical maximum efficiency of about 75%. However under realistic operating conditions they generally operate at about 50% efficiency which, when coupled to inherent efficiencies of less than 60% in an associated high voltage power supply, result in overall efficiency levels of less than 30%. In order to overcome the foregoing, the practice of this invention preferrably utilizes a Class D switching power amplifier which has inherent efficiency in excess of 90% to provide an overall efficiency in excess of 50% when operating in the fluoroscopic mode and with substantially higher efficiencies when operating in the radiographic mode.

As hereinbefore pointed out the hand portable x-ray system described described is characterized by the utilization of a high voltage power supply of diminutive size and unique design that is disposed within the hand-held device and preferably located immediately adjacent the x-ray tube housing assembly. As heretofor discussed relative to the low voltage power conversion and amplification equipment, the efficiency of electrical energy conversion is a prime concern in order to minimize heat generation and the problems attendant thereto, as well as to maximize the useful life of the battery power source. The high voltage power supply operates to convert the output of the low voltage power amplifier, typically 20 kiloherz AC at up to 30 volts RMS into a DC voltage of up to 80 kilovolts and typically delivering a current of 1 milliamp. The means to accomplish this broadly comprise a high voltage transformer adapted to convert the 20 KHz low voltage signal to a considerably higher voltage level and an associated long chain series multiplying means to multiply and rectify the transformer amplified high voltage AC signal to the desired high DC voltage. As recognized by those skilled in the high voltage art, the efficiency of long chain series multiplying means degrades rapidly as the number of stages in the multiplier increases and also as the DC current level increases, unless the value of the capacitors included in the chain increases accordingly.

Figure 6:
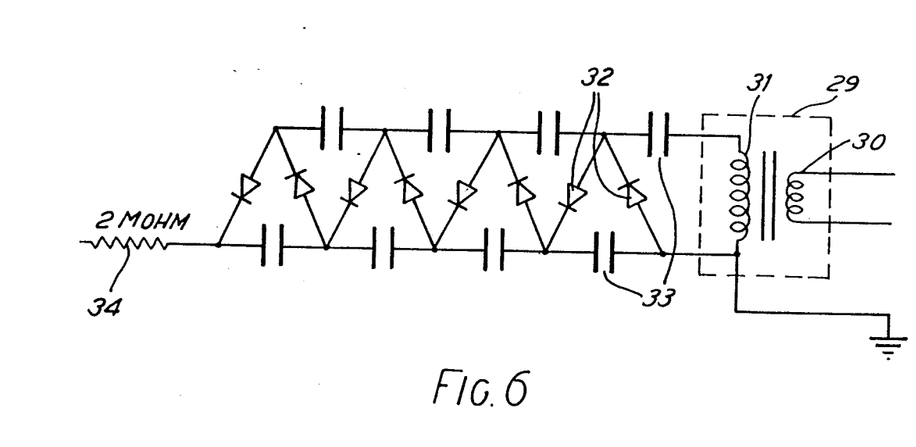
FIG. 6 is a schematic circuit diagram of a suitable diminutively sized high voltage power supply employing high voltage transformer and long chain series multiplying means.

Referring now to FIG. 6, there is provided a circuit diagram of a preferred high voltage multiplier circuit of diminutive physical size. The input transformer 29 includes a low loss ferrite EE core, suitably of Magnetics Inc. P material, with a center leg cross-section of 0.90 square centimeters. The primary 30 of the transformer 29 contains 9 turns and the secondary thereof 31, contains 3200 turns in 5 isolated segments. Such a transformer, suitably impregnated and encapsulated, can produce a peak voltage in excess of 10 kilovolts. The high turns ratio employed therein results in a large capacitance reflected to the primary 30 of the transformer necessitating a substantial center leg gap to prevent drawing high quadrature currents from the primary source. We have found that a four stage multiplier, as shown, is optimum for this application, with each stage comprising a pair of high voltage diodes 32 and a pair of high voltage capacitors 33. Each capacitor and diode is subject to a voltage of twice the peak transformer voltage and accordingly in this application must be constucted to withstand 20 kilovolts. With presently available state of the art components, the utilization of peak to peak AC voltages in excess of 20 kilovolts in order to reduce the number of stages will result, in a significant increase in the size of the capacitors and, accordingly, in the size and weight of the power supply. Conversely, reducing the voltage per stage requires an increase in the number of stages and concomittantly results in significant loss of efficiency and regulation unless the value of the capacitors is again increased substantially with an attendant increase in size. We have found it basically impractical to operate with more than six stages of voltage multiplication and highly desirable to utilize no more than four stages thereof. The output of the illustrated power supply is connected through a limiting resistor 34 of high value, suitably in the order of 2 to 10 megohms, which serves to protect the components therein from high surge currents in the event of external arc occurrence. In the operating enviroment, the entire power supply is suitably wrapped and encapsulated using materials of high dielectric strength to withstand voltage breakdown and is further coated with a suitable conducting paint to prevent outside static buildup and to shield other electronic components in the system from the high electric fields extend therein. Power supplies of the character described capable of producing 85 kilovolts at 1 milliamp have been constructed with a weight of 300 gms and a physical size of approximately 3cm×4cm×15cm.

Having thus described my invention, I claim:

1. Hand portable and readily moveable, light weight and diminutive diagnostic apparatus for the provision of a permanent record visable image of portions of a human body responsive to transmission of x-radiation through said body portions comprising manually manipulable frame means for supporting a source of x-radiation and a radiation responsive image producing means in a predetermined spaced apart relation not exceeding 50 centimeters therebetween to permit interposition of a selected portion of a human body to be examined therebetween, said source of x-radiation consisting of an x-ray tube having a focal spot not exceeding 1 millimeter square in area for emitting a beam of x-rays centered about a predetermined axis, low voltage amplification means disposed within said frame means adapted to provide a high frequency low output voltage of up to 30 volts RMS, high voltage generation means disposed within said frame means adjacent to said source of x-radiation adapted to convert the high frequency output of said low voltage amplification means into a DC voltage output of up to 85 kilovolts for application to said source of x-radiation, said image producing means including an x-radiation responsive cassette containing an unexposed photographic film for converting x-radiation which passes through said interposed body portion and then uninterruptedly impinges onto said cassette for forming a permanent visable and radiation responsive photographic image thereof, and said image producing means including independent x-radiation to visable light conversion screen means for producing a viewable permanent photographic image at a resolution level of at least 3.5 line pairs per millimeter.

2. The combination as set forth in claim 1 wherein said high voltage generation means includes an input transformer to elevate the magnitude of the low voltage high frequency input and a long chain series multiplier to multiply and rectify the transformer amplified input voltage into a high DC voltage output.

3. Hand portable diagnostic apparatus as set forth in claim 1, including means operative in response to the positioning of said photographic image producing means in predetermined spatial relation with said x-radiation source for limiting the x-ray tube electron beam current to a value intermediate 500 microamperes and 3 milliamperes.

4. Hand portable diagnostic apparatus as set forth in claim 1 including means for exposing said screen means, absent interposition of an object to be examined, to radiation exposure in excess of 2.5 R/min but not exceeding 15 R/min.

5. Hand portable and readily moveable, light weight and diminutive diagnostic apparatus for the provision of a transitory visable image of portions of a human body responsive to transmission of x-radiation through said body portions comprising manually manipulable frame means for supporting a source of x-radiation and radiation responsive image producing means in a predetermined spaced apart relation not exceeding 50 centimeters therebetween to permit interposition of a selected portion of a human body to be examined therebetween, said source of x-radiation consisting of an x-ray tube having a focal spot not exceeding 1 millimeter square in area for emitting a beam of x-rays centered about predetermined axis, low voltage amplification means disposed within said frame means adapted to provide a high frequency low output voltage of up to 30 volts RMS, high voltage generation means disposed within said frame means adjacent to said source of x-radiation adapted to convert the high frequency output of said low voltage amplification means into a DC voltage output of up to 85 kilovolts for application to said source of x-radiation, said image producing means including means for converting x-radiation passing through said interposed selected body portion into a transitory fluoroscopic visable image thereof, and said image producing means including independent x-radiation to visable light conversion screen means for producing a viewable transitory fluroroscopic image at a resolution level of at least 3.5 line pairs per millimeter.

6. The combination as set forth in claim 5 wherein said high voltage generation means includes an input transformer to elevate the magnitude of the low voltage high frequency input thereto and a long chain series multiplier to multiply and rectify the transformer amplified input voltage into a high DC voltage output.

7. Hand portable diagnostic apparatus as set forth in claim 5 including means operative in response to the disposition of said fluoroscopic image producing means in predetermined spatial relation with said x-radiation source for limiting the x-ray tube electron beam current to a value intermediate 50 microamperes and 300 microamperes.

8. Hand portable diagnostic apparatus as set forth in claim 5 including means responsive to the presence of said image producing means for exposing said screen means, absent interposition of an object to be examined, to radiation exposure in excess of 0.15 R/min but not exceeding 2.0 R/min.

* * * * *